United States Patent [19]

Kross et al.

[11] Patent Number: 5,100,652

[45] Date of Patent: * Mar. 31, 1992

[54] DISINFECTING ORAL HYGIENE COMPOSITIONS AND PROCESS FOR USING THE SAME

[75] Inventors: Robert D. Kross, Bellmore; Robert Lofaro, North Babylon; Carol A. Zamojcin, Floral Park, all of N.Y.

[73] Assignee: Alcide Corporation, Norwalk, Conn.

[*] Notice: The portion of the term of this patent subsequent to Jan. 22, 2008 has been disclaimed.

[21] Appl. No.: 489,716

[22] Filed: Feb. 28, 1990

Related U.S. Application Data

[63] Continuation of Ser. No. 21,460, Mar. 4, 1987, abandoned, which is a continuation-in-part of Ser. No. 450,009, Apr. 10, 1986, abandoned, which is a continuation-in-part of Ser. No. 790,436, Oct. 23, 1985, abandoned, which is a continuation of Ser. No. 591,787, Mar. 21, 1984, abandoned.

[51] Int. Cl.$^5$ .................. A61K 7/20; A61K 33/14
[52] U.S. Cl. ................................ 424/53; 424/661
[58] Field of Search ...................... 424/53, 661

[56] References Cited

U.S. PATENT DOCUMENTS

| | | | |
|---|---|---|---|
| Re. 31,779 | 12/1984 | Alliger | 252/187.23 |
| 2,332,180 | 10/1943 | Soule | 424/149 |
| 2,484,637 | 10/1949 | Mattocks, Jr. et al. | 167/63 |
| 2,550,622 | 4/1951 | Taub | 167/63 |
| 2,701,782 | 2/1955 | Cutler | 167/56 |
| 2,726,982 | 12/1955 | Ochs et al. | 167/58 |
| 3,186,869 | 6/1965 | Friedman | 117/138.8 |
| 3,518,343 | 6/1970 | Welsh et al. | 424/53 |
| 3,663,716 | 5/1972 | Stolar | 424/243 |
| 3,754,079 | 8/1973 | Callerame | 423/479 |
| 4,104,190 | 8/1978 | Hartshorn | 424/149 |
| 4,330,531 | 5/1982 | Alliger | 424/149 |
| 4,585,482 | 4/1986 | Tice et al. | 424/149 |
| 4,690,772 | 9/1987 | Tell et al. | 424/149 |
| 4,696,811 | 9/1987 | Ratcliff | 424/149 |

FOREIGN PATENT DOCUMENTS 959238 12/1974 Canada.
158180 6/1972 New Zealand.

OTHER PUBLICATIONS

Chemical Abstracts No. 80:74331g (1974).
Gordon et al., "The Chemistry of Chlorine Dioxide", *Prog. Inorg. Chem.*, 15:201, 1972.
Derwent Abstract No. 25988 K/11 (Feb. 3, 1981).

*Primary Examiner*—Leonard Schenkman
*Attorney, Agent, or Firm*—Seed and Berry

[57] ABSTRACT

The present invention provides low concentration chlorous-acid generating compositions useful for oral hygiene. The compositions are effective oral disinfectants which do not have the strong unpleasant taste of chlorine and are useful in reducing plaque. The invention also concerns processes for making the inventive compositions and methods for using the same.

26 Claims, No Drawings

DISINFECTING ORAL HYGIENE COMPOSITIONS AND PROCESS FOR USING THE SAME

CROSS REFERENCE TO RELATED APPLICATIONS

This application is a continuation of U.S. application Ser. No. 07/021,460, filed Mar. 4, 1987, now abandoned; which is a continuation-in-part of U.S. application Ser. No. 06/850,009, filed Apr. 10, 1986, now abandoned; which is a continuation-in-part of U.S. application Ser. No. 06/790,436, filed Oct. 23, 1985, now abandoned; which is a continuation of U.S. application Ser. No. 06/591,787, filed Mar. 21, 1984, now abandoned. The entire disclosure of these earlier applications is hereby incorporated by reference.

BACKGROUND OF THE INVENTION

This invention relates to disinfecting compositions useful as oral hygiene compositions such as a mouthwash, toothpaste, lozenge, chewing gum, or the like. The inventive compositions disinfect by means of a chlorous acid generating composition.

While chlorine-liberating compounds have germicidal and deodorant properties, their characteristic taste and odor make them unpleasant for use in oral hygiene compositions such as mouthwashes. Other oral hygiene compositions, some commercially available, while pleasant tasting, are ineffective to reduce dental plaque as well as control gingivitis and periodontitis.

The search has continued for new and improved oral hygiene compositions which are both pleasant tasting and effective in reducing dental plaque as well as control gingivitis and periodontitis. This invention was made as a result of that search.

OBJECTS AN SUMMARY OF THE INVENTION

Accordingly, it is a general object of the present invention to avoid or substantially alleviate the above-identified problems of the prior art.

A more specific object of the present invention is to provide improved oral hygiene compositions useful in reducing dental plaque.

A further object of the present invention is to provide oral hygiene compositions which are pleasant tasting yet effective to reduce dental plaque and control gingivitis and periodontitis.

An additional object of this invention is to provide a method for producing these oral hygiene compositions.

Yet another object of this invention is to provide a method for disinfecting the mouth comprising treating the mouth with these oral hygiene compositions.

Other objects and advantages of the present invention will become apparent from the following summary of the invention and description of the preferred embodiments.

The present invention provides, in one aspect, a disinfectant oral hygiene compositions for reducing dental plaque and controlling gingivitis and periodontitis. This composition comprises (a) a flavoring agent acceptable for oral hygiene compositions, (b) an aqueous solution containing a suitable amount of a protic acid, and (c) an amount of a metal chlorite such that the chlorite ion concentration in the form of chlorous acid is no more than about 15 percent by weight of the total amount of chlorite ion concentration. The composition contains substantially no lactic acid.

In another aspect, the present invention provides a process for producing these disinfectant oral hygiene compositions. This process comprises admixing (a) a flavoring agent acceptable for oral hygiene compositions, (b) from about 0.03 to about 0.3 percent by weight of a chlorine dioxide liberating compound based upon the total weight of the composition, and (c) a suitable amount of an organic acid having a pK of from about 2.8 to about 4.2. The composition contains substantially no lactic acid.

In yet another aspect, the present invention provides a process for reducing dental plaque in the mouth. This process comprises treating the mouth with a composition which comprises (a) a flavoring agent acceptable for oral hygiene compositions, (b) from about 0.03 to about 0.3 percent by weight of a chlorine dioxide liberating compound based upon the total weight of the composition, and (c) a suitable amount of an organic acid having a pK of from about 2.8 to about 4.2. The composition contains substantially no lactic acid.

The disinfecting compositions of this invention disinfect by means of a chlorous acid generating composition. The composition comprises a flavoring agent, a suitable amount of a carboxylic acid, and a suitable amount of a metal chlorite. The chlorite ion concentration in the form of chlorous acid is no more than about 15 percent by weight of the total amount of chlorite ion concentration.

The oral hygiene formulations of this invention contain low concentrations of chlorous acid generating compounds which are extremely effective as oral disinfectants. These compositions provide effective mouthwashes, toothpastes and other oral disinfecting compositions without the strong characteristic unpleasant taste of chlorine.

DETAILED DESCRIPTION OF THE PREFERRED EMBODIMENTS

The oral hygiene compositions of this invention comprise a flavoring agent suitable for use in an oral hygiene composition, a suitable amount of a carboxylic acid, and a suitable amount of a metal chlorite. The concentrations of chlorite and acid are relatively low and are such that the amount of chlorite in the form of chlorous acid is no more than about 15 percent by weight of the total chlorite ion concentration in solution. Typically the amount of the chlorite in the form of chlorous acid is no more than about 10 percent by weight of the total chlorite ion concentration in solution.

The percent by weight of chlorite and chlorous acid may be calculated from the ionization constant of chlorous acid and the amount of hydrogen ion in solution produced by the partial ionization of the carboxylic acid. Thus the hydrogen ion concentration, [H+], in a solution of the carboxylic acid, HA, of known molar concentration and whose ionization constant is $K_A$, may be calculated from the following relationship:

$$K_A = \frac{[H^+][A^-]}{[HA]}$$

This same relationship may be applied to calculate the relative chlorite and chlorous acid concentrations where the ionization constant for chlorous acid is $1.1 \times 10^{-2}$. That is:

$$1.1 \times 10^{-2} = \frac{[H^+][ClO_2]}{[HClO_2]}$$

where the hydrogen ion concentration, [H+], is the quantity already determined by ionization of the known amount of the carboxylic acid, HA. This calculation is well known to those skilled in this art.

The compositions of this invention provide a metastable chlorous acid composition formed from relatively small amounts of chlorite and acid. This composition is capable of generating chlorine dioxide over a long period of time at continuing levels of effectiveness. As chlorine dioxide forms, more of the chlorite converts to chlorous acid by interacting with hydrogen ions further generated by ionization of the carboxylic acid.

The compositions of this invention are therefore different from many prior art chlorine dioxide generating compositions which consist of relatively high concentrations of chlorite and acid. Prior art chlorine dioxide containing compositions were not used as mouthwashes or toothpastes and result in the rapid conversion of chlorous acid to chlorine dioxide. The rate of chlorine dioxide formation depends on the sum of the square of chlorous acid concentration and the product of chlorous acid and chlorite concentrations according to the equation $$\frac{d[ClO_2]}{dt} = K_1[HClO_2]^2 + K_2[HClO_2][ClO_2^-]$$

See Gordon. "The Chemistry of Chlorine Dioxide", 15 Prog. Inorg. Chem. 201 (1972).

Thus the rate at which chlorine dioxide forms depends exponentially on the amount of chlorite ion which is converted to chlorous acid and the amount of chlorite ion present.

In certain embodiments of the invention, the chlorous acid generating composition comprises an aqueous solution containing generally from about 0.01 to about 1, typically from about 0.02 to about 0.5, and preferably from about 0.03 to about 0.3 percent by weight of metal chlorite and a suitable amount of an organic acid having a pK of from about 2.8 to about 4.2. The pH of this composition is generally less than about 7, typically from about 2.2 to about 7.0.

In yet another embodiment of this invention, even lower concentrations of chlorite and acid may be used in the composition. These compositions comprise an aqueous solution containing generally up to about 0.4, and typically from about 0.0001 to about 0.03 percent by weight of metal chlorite, and a suitable amount of acid having a pK of from about 2.8 to about 4.2. The pH of the composition is generally less than about 7, typically from about 2.2 to about 7.0.

In certain embodiments of the invention, the carboxylic acid is an alpha-hydroxy carboxylic acid. In preferred embodiments, the alpha-hydroxy carboxylic acid has the formula

(I)

wherein $R^1$ and $R^2$ may be the same or different and may be selected from the group consisting of hydrogen, methyl, —CH$_2$COOH, —CH$_2$OH, —CHOHCOOH and —C$_6$H$_5$.

Optionally the compositions of the invention may contain either a suitable amount of a compound containing vicinal hydroxy groups or an amount of a water soluble chloride in a significant molar excess to the chlorite, or both. These optional ingredients may facilitate the formation of chlorine dioxide from chlorous acid and are thus useful in rapidly disinfecting compositions where an increased rate of chlorine dioxide formation is desired while maintaining a low concentration of chlorite and acid.

The metal chlorite useful in the present composition may more generally be described as a chlorine dioxide liberating compound. By "chlorine dioxide liberating compound" is meant any compound which, when appropriately treated, effects the production of chlorine dioxide as a result of a change in the valence state of the chlorine atom from +3 to 4. While any chlorine dioxide liberating compound may be used, water-soluble chlorites are preferred because they are readily available and inexpensive. Typical water-soluble chlorites include metal chlorites, such as alkali metal chlorites and alkaline earth metal chlorites. Sodium chlorite and potassium chlorite are preferred. Sodium chlorite is particularly preferred.

The flavoring agents useful in the compositions of this invention include any flavoring agent or mixture of flavoring agents acceptable in oral hygiene compositions. Such flavoring agents are well known to those skilled in this art and include 1-carvone (mint flavor), peppermint oil, aspartame, saccharin, wintergreen oil, cinnamon oil, clove oil, menthol, thymol, eucalyptol, oil of sassafras, oil of anise, dextrose and levulose, and other flavoring agents well known to those skilled in this art.

The term "oral hygiene compositions" is meant to include any composition which is used in the mouth in order to promote oral hygiene. These compositions may be in the form of a mouthwash, toothpaste, chewing gum, lozenge, or the like.

These compositions may be in the form of aqueous solutions, as in a mouthwash composition, gels, as in toothpaste or dentifrice compositions, solids, as in lozenges, or combined with fillers, as in a chewing gum composition.

The compositions of this invention may contain other additives such as chelating agents (e.g., Na$_4$EDTA), or preservatives (e.g., sodium benzoate). The identity and amount of the other additives will depend upon the type of oral hygiene composition and its end use. Such additives are well known to those skilled in the art. Suitable penetrants, astringents, deodorants, and other therapeutic or preventive compounds may be added. Dentrifices or toothpaste compositions according to the invention may also contain humectants, binders sudsing agents, abrasive polishing materials, and thickening agents.

The amount of chlorine dioxide liberating compound that may be used in this composition may be generally from about 0.01% to about 1%, typically from about 0.02% to about 0.05%, and preferably from about 0.03% to about 0.3% by weight of the total composition (including the application medium).

At chlorite ion levels higher than about 0.5%, the concentration of chlorous acid formed upon admixture of a carboxylic acid may be in excess of that required for the formation of a metastable chlorous acid solution. These higher concentrations of chlorous acid would cause the formation of chlorine dioxide, through the degradation of chlorous acid at too rapid a rate.

Any acid of low toxicity may be used in the compositions of the invention so long as the chlorite ion concentration limits described above and the degree of conversion to chlorous acid are met. Preferably carboxylic acids are used. Preferred carboxylic acids include citric, malic, tartaric, glycolic, mandelic or other structurally similar acids as described in Formula I hereinabove.

The pK of these carboxylic acids may be generally from about 2.8 to about 4.2, and preferably from about 3.0 to about 4.0.

The amount of carboxylic acid used in these compositions should be sufficient to lower the pH of the composition to less than about 7, typically from about 2.5 to about 6, and preferably from about 3.0 to about 5.0. Furthermore, this amount may be generally from about 0.01% to about 3%, typically from about 0.05% to about 2%, and preferably from about 0.1% to about 1% by weight of the total composition (including the application medium).

The amount of flavoring agent useful in this invention may vary widely but is generally from about 0.01 to about 5, typically from about 0.02 to about 2, and preferably from about 0.05 to about 1 percent by weight based upon the total weight of the composition.

A suitable amount of a vicinal dihydroxy or polyhydroxy compound may also be added to the compositions of the present invention. The use of such compositions enables one to produce compositions according to the invention which are more rapidly effective in higher pH ranges. The use of these vicinal dihydroxy or polyhydroxy compounds also allows for the use of compositions according to the invention which contain a much lower acid concentration than that which is needed if the vicinal polyhydroxy compound comprising at least two vicinal hydroxy groups is absent.

Vicinal polyhydroxy compounds which contain at least two vicinal hydroxy groups are well known to those skilled in this art and include dextrose and other sugars, glycerin, sorbitol, and inositols. In other embodiments sugars with vicinal hydroxy groups in the cis configuration such as galactose, mannose, and ribose may be used.

The use of such vicinal polyhydroxy compounds, particularly those with cis-vicinal hydroxy groups, in conjunction with the chlorine dioxide liberating compound and carboxylic acid results in a synergistic composition. The vicinal dihydroxy or polyhydroxy compound catalyzes the formation of chlorine dioxide from chlorous acid. For example, the rate of formation of the active chlorine dioxide entity using a composition comprising sodium chlorite and mandelic acid is substantially enhanced by the addition of a relatively insubstantial amount of a vicinal polyhydroxy compound. Thus, the use of as little as 0.1% ribose in the composition substantially enhances the rate of formation of the active entity vis-a-vis a composition containing only sodium chlorite and one of the organic acids discussed hereinabove.

Stated otherwise, a composition containing the vicinal polyhydroxy compound may be prepared having substantially the same initial germ-killing efficacy in a specified time period as a composition which does not contain the vicinal polyhydroxy compound even though the composition containing the polyhydroxy compound contains substantially much less organic acid and sodium chlorite. However, such activation of the system results in a more rapid depletion of the chlorite ion in the composition, so that the germ-killing activity at a later time period would be less. The vicinal polyhydroxy compounds may also serve another purpose in the composition in that it may act as a sweetener or enhance the solubility of the flavoring agents.

The amount of vicinal polyhydroxy compound containing at least two vicinal hydroxy groups may vary widely, but in the present invention there is employed generally less than about 20%, typically from about 0.1% to about 10%, and preferably from about 0.2% to about 5% by weight of the total composition.

Alternatively, or in addition, the composition may contain a large excess of chloride ion in the form of an alkali or an alkaline earth metal salt. The excess may be from about a 10 to about a 100 fold excess by weight of chloride ion over total chlorite ion concentration. Large excesses of chloride ion in acid solutions (below a pH of about 7) cause the chlorite ion to decompose in an accelerated manner, via the formation of chlorous acid to form chlorine dioxide. In a preferred embodiment of the invention where rapid disinfection is required, the composition contains both a high excess of chloride ion and a sufficient amount of a vicinal polyhydroxy compound comprising at least two vicinal hydroxy groups.

The chlorine dioxide liberating compound is generally kept separate from the organic acid prior to use in order to avoid premature reaction of the ingredients. The flavoring agent may be combined with either the organic acid or the chlorine dioxide liberating compound, or both, prior to their admixture.

The oral hygiene compositions of this invention result in improved bactericidal, fungicidal, virucidal and taste properties over presently available commercial oral hygiene compositions and aid in dental plaque reduction.

The present invention also provides a process for producing disinfectant oral hygiene compositions. This process comprises admixing (a) a flavoring agent acceptable for oral hygiene compositions, (b) from about 0.03 to about 0.3% by weight of a chlorine dioxide liberating compound based upon the total weight of the composition, and (c) a suitable amount of an organic acid which has a pK of from about 2.8 to about 4.2. The composition contains substantially no lactic acid.

The present invention also provides a process for reducing dental plaque as well as controlling gingivitis and periodontitis in the mouth. This process comprises treating the mouth with an oral hygiene composition. The composition comprises (a) a flavoring agent acceptable for use in the mouth, (b) from about 0.03 to about 0.3 of a chlorine dioxide liberating compound based upon the total weight of the composition, and (c) a suitable amount of an organic acid having a pK of from about 2.8 to about 4.2. The composition contains substantially no lactic acid.

The present invention is illustrated by the following Examples. All parts and percentages in the Examples as well as in the specification and the claims are by weight unless specified otherwise.

EXAMPLE I

This Example illustrates the preparation of a mouthwash according to the present invention.

A first solution in prepared by dissolving 0.4 grams of technical grade sodium chlorite, 0.17 grams of powdered $Na_4EDTA \cdot 4H_2O$, 0.5 grams of 1-carvone (mint flavor), and the appropriate amount of a compatible food grade yellow dye in 500 milliliters of aqueous solution. A second solution is prepared by dissolving 1.375 grams of anhydrous citric acid and the appropriate amount of FD&C Blue #1 in a batch of 500 milliliters of a 10 percent by weight aqueous solution of glycerin.

The two solutions are mixed, preferably just prior to use, in substantially equal amounts and the mixture is used in the normal manner as a mouthwash.

EXAMPLE II

This Example also illustrates the preparation of a mouthwash according to the present invention.

A first aqueous solution of 0.25% sodium chlorite and 0.10% NaOH in deionized water is prepared.

A second aqueous activator solution is prepared of 0.75% malic acid, 10.00% glycerine USP, 0.05% sodium benzoate, 0.50% Equal (aspartame diluted with dextrose and corn syrup solids), 0.03% FD&C Blue #1 (0.3% solution), and 0.40% Wintergreen Flavor (BBA), in deionized water.

The two solutions are mixed, preferably just prior to use in substantially equal amounts, and the mixture is used in the normal manner as a mouthwash.

EXAMPLE III

This Example illustrates the ability of a composition of the present invention to reduce dental plaque and control gingivitis and periodontitis.

Mouthwash compositions according to the invention were used in a five day triple-crossover plaque reduction test. In this test 18 human subjects were divided into three groups of six subjects each. The teeth of each subject were scraped free of plaque immediately prior to the commencement of each five day period.

Each group was subjected to three five day periods of treatment with the following formulations (a) placebo, (b) low potency mouthwash formulation, and (c) high potency mouthwash formulation. The sequence of the treatments per group were selected in a random fashion. During the five day period the subjects rinsed with the formulation twice daily, i.e., in the morning and afternoon. The subjects did not brush their teeth or perform any other oral hygiene procedures. The same treatment procedure was followed for all three of the formulations. Plaque scores after each five day period were determined by a modified Quigley-Hein index.

The placebo was formulated so that it had substantially the same perceived acidity as the other two formulations. The placebo formulation comprised an aqueous solution of 0.27% citric acid, 0.08% sodium chloride, 0.05% 1-carvone, 0.09% FD&C Green #3 (5000 ppm solution), 0.03% FD&C Yellow #5 (5000 ppm solution), and 5.0% glycerin.

The compositions were formulated in two parts A and B. Equal volumes of the two parts were mixed immediately before rinsing. The percent compositions of parts A and B of the high potency and low potency formulations were as follows:

| INGREDIENT | HIGH POTENCY | LOW POTENCY |
|---|---|---|
| Part A | | |
| Sodium chlorite (79%) | 0.32 | 0.08 |
| 1-Carvone | 0.10 | 0.10 |
| FD&C Green #3 (5000 ppm soln) | 0.18 | 0.18 |
| 1N Sodium hydroxide | 0.10 | 0.10 |
| Water | q.s. | q.s. |
| Part B | | |
| Malic acid | 0.75 | 0.275 |
| Sodium benzoate | 0.05 | 0.05 |
| Glycerin | 10.00 | 10.0 |
| FD&C Yellow #5 (5000 ppm soln) | 0.06 | 0.06 |
| Water | q.s. | q.s. |

The average plaque scores of the subjects listed below show that the mouthwash compositions of this invention were effective in substantially reducing dental plaque.

| | Score (average) | % Reduction |
|---|---|---|
| Placebo | 3.82 | — |
| Low potency | 3.35 | 12.3 |
| High potency | 2.47 | 35.3 |

EXAMPLE IV

This Example illustrates the preparation of a toothpaste composition according to the present invention.

There is prepared a two-part disinfectant toothpaste composition according to the invention having a first base paste or gel and a second activator paste or gel.

The formulations of the two toothpaste parts on a percent weight to weight basis are as follows:

| TOOTHPASTE | |
|---|---|
| | % W/W |
| BASE | |
| Poly(sulfonic Acid) | 45.0 |
| Sodium hydroxide, 1N | 40.0 |
| Bentonite | 2.0 |
| Sodium lauryl sulfate | 1.0 |
| Titanium dioxide | 1.0 |
| Silica, amorphous | 0.5 |
| Sodium chlorite | 1.0 |
| Water | q.s |
| ACTIVATOR | |
| Glycerin | 10.0 |
| Magnesium aluminum silicate | 5.0 |
| Hydroxyethylcellulose | 2.0 |
| Malic acid | 1.5 |
| Flavor, wintergreen | 0.4 |
| FD & C Blue #1 (0.5% soln) | 0.06 |
| Sodium benzoate | 0.05 |
| Sodium saccharin | 0.05 |
| Water | q.s. |

The pH of the composition resulting from the mixture of substantially equal portions of the base and activator gels of the above formulation is about 4.15.

The base gel and the activator gel are preferably stored separately prior to use, e.g., in a double compartment tube. The two gels are mixed preferably just prior to use in substantially equal amounts and the mixture is used in the normal manner as a toothpaste. Alternatively, substantially equal portions of the gels are placed in the mouth and mixed by the brushing action while the subject brushes his or her teeth.

The principles, preferred embodiments and modes of operation of the invention have been described in the foregoing specification. The invention which is intended to be protected herein, however, is not to be construed as limited to the particular forms disclosed, since these are to be regarded as illustrative rather than restrictive. Variations and changes may be made by those skilled in this art without departing from the spirit of this invention.

EXAMPLE V

An evaluation was made of the microbiocidal effectiveness of the High Potency mouthwash (0.32% Sodium chlorite—Part A; 0.75% Malic acid—Part B) in Example III, vs. that of 0.2% chlorhexidine digluconate. The 0.2% Chlorhexidine digluconate solution is the recommended reference standard by which other oral hygiene germicides should be measured. The procedure employed was based on the method in the FDA OTC Oral Health Care Monograph (Federal Register, Vol. 47, No. 101, May 25, 1982, pages 22890-22900). The test organisms were:

Candida albicans ATCC 18804 (American Type Culture Collection, Rockville, Md.)
Actinobacillus actinomvcetemcomitans Forsyth Clinic Isolate #Y4
Streptococcus mutans ATCC 25175

The microorganisms were grown in Brain Heart Infusion, and subcultured for two successive days at 37° C. Two ml of a 50:50 mix of each test organism in sterile fetal calf serum was added to 8 ml of the mouthwash formulation, and triplicate aliquots of the inoculated test formulation were removed at 30 and 60 second for subculture. C. albicans was grown and subcultured aerobically; all other organisms, anaerobically. The High Potency test solutions were neutralized first in fluid thioglycolate medium, and further neutralized in the plate count agar. The chlorhexidine digluconate control solutions were only neutralized in the enumeration agar. Results obtained were as follows:

| Formulation | Test Organism | Average Microbial Log Reduction* | |
|---|---|---|---|
| | | 30 Sec. Exp. | 60 Sec. Exp. |
| High Potency | C. albicans | 3.2 | 3.0 |
| | Actinobacillus | 7.5 | 7.5 |
| | Strep. mutans | 3.5 | 4.3 |
| Chlorhexidine | C. albicans | 3.2 | 3.3 |
| digluconate, 0.2% | Actinobacillus | 6.6 | 6.3 |
| | Strep. mutans | 3.0 | 3.0 |

*Average of three results.

The High Potency Formulation shows a microbiocidal efficacy equal to or greater than of chlorhexidine digluconate at the 0.2% level.

These microbiocidal data strongly indicate that these formulations will not only be helpful in reducing dental plaque formation, but also would inhibit the onset and severity of gingivitis and other associated oral disorders such as periodontitis which could lead to eventual tooth loss.

I claim:

1. A disinfectant oral hygiene composition comprising (a) a flavoring agent acceptable for oral hygiene compositions, (b) an aqueous solution containing from about 0.01% to about 3% by weight of an organic acid based upon the total weight of the composition, the organic acid having a pK of from about 2.8 to about 4.2, and wherein the organic acid is not lactic acid or citric acid, and (c) from about 0.0001% to about 0.4% by weight of a metal chlorite based upon the total weight of the composition, such that the chlorite ion concentration in the form of chlorous acid is no more than about 15% by weight of the total amount of chlorite ion concentration.

2. A disinfectant oral hygiene composition comprising (a) a flavoring agent acceptable for oral hygiene compositions, (b) an aqueous solution containing from about 0.05% to about 3% by weight of citric acid based upon the total weight of the composition, and (c) from about 0.001% to about 0.4% by weight of a metal chlorite based upon the total weight of the composition, such that the chlorite ion concentration in the form of chlorous acid is no more than about 15% by weight of the total amount of chlorite ion concentration.

3. A disinfectant oral hygiene composition comprising (a) a flavoring agent acceptable for oral hygiene compositions, (b) an aqueous solution containing a compound which contains at least two vicinal hydroxy groups, (c) from about 0.01% to about 3% by weight of an organic acid based upon the total weight of the composition, the organic acid having a pK of from about 2.8 to about 4.2, and wherein the organic acid is not lactic acid or citric acid, and (d) from about 0.0001% to about 0.4% by weight of a metal chlorite based upon the total weight of the composition, such that the chlorite ion concentration in the form of chlorous acid is no more than about 15% by weight of the total amount of chlorite ion concentration.

4. A disinfectant oral hygiene composition comprising (a) a flavoring agent acceptable for oral hygiene compositions, (b) an aqueous solution containing a compound which contains at least two vicinal hydroxy groups, (c) from about 0.05% to about 3% by weight of citric acid based upon the total weight of the composition, and (d) from about 0.0001% to about 0.4% by weight of a metal chlorite based upon the total weight of the composition, such that the chlorite ion concentration in the form of chlorous acid is no more than about 15% by weight of the total amount of chlorite ion concentration.

5. The composition of any one of claims 1 through 4 wherein the metal chlorite is sodium chlorite.

6. The composition of any one of claims 1 or 3 wherein the organic acid is selected from he group consisting of malic acid, tartaric acid, glycolic acid, mandelic acid, salicylic acid, carbonic acid, and combinations thereof.

7. The composition of any one of claims 1 or 3 wherein the organic acid is malic acid.

8. The composition of any one of claims 1 or 3 wherein the organic acid is tartaric acid.

9. The composition of any one of claims 1 or 3 wherein the organic acid is glycolic acid.

10. The composition of any one of claims 1 or 3 wherein the organic acid is mandelic acid.

11. The composition of any one of claims 1 or 3 wherein the organic acid is salicylic acid.

12. The composition of any one of claims 1 or 3 wherein the organic acid is carbonic acid.

13. The composition of any one of claims 1 through 4 wherein the flavoring agent is selected from the group consisting of 1-carvone, aspartame, saccharin, peppermint oil, wintergreen oil, cinnamon oil, clove oil, menthol, thymol, eucalyptol, and combinations thereof.

14. A process for reducing dental plaque in a mouth comprising treating the mouth with a composition comprising (a) a flavoring agent acceptable for oral hygiene compositions, (b) an aqueous solution containing from about 0.01% to about 3% by weight of an organic acid based upon the total weight of the composition, the organic acid having a pK of from about 2.8 to about 4.2, and wherein the organic acid is not lactic acid or citric acid, and (c) from about 0.0001% to about 0.4% by weight of a metal chlorite based upon the total weight of the composition, such that the chlorite ion concentration in the form of chlorous acid is no more than about 15% by weight of the total amount of chlorite ion concentration.

15. A process for reducing dental plaque in a mouth comprising treating the mouth with a composition comprising (a) a flavoring agent acceptable for oral hygiene compositions, (b) an aqueous solution containing from about 0.05% to about 3% by weight of an organic acid based upon the total weight of the composition, and (c) from about 0.0001% to about 0.4% by weight of a metal chlorite based upon the total weight of the composition, such that the chlorite ion concentration in the form of chlorous acid is no more than about 15% by weight of the total amount of chlorite ion concentration.

16. A process for reducing dental plaque in a mouth comprising treating the mouth with a composition comprising (a) a flavoring agent acceptable for oral hygiene compositions, (b) an aqueous solution containing a compound which contains at least two vicinal hydroxy groups, (c) from about 0.01% to about 3% by weight of an organic acid based upon the total weight of the composition, the organic acid having a pK of from about 2.8 to about 4.2, and wherein the organic acid is not lactic acid or citric acid, and (d) from about 0.0001% to about 0.4% by weight of a metal chlorite based upon the total weight of the composition, such that the chlorite ion concentration in the form of chlorous acid is no more than about 15% by weight of the total amount of chlorite ion concentration.

17. A process for reducing dental plaque in a mouth comprising treating the mouth with a composition comprising (a) a flavoring agent acceptable for oral hygiene compositions, (b) an aqueous solution containing a compound which contains at least two vicinal hydroxy groups, (c) from about 0.05% to about 3% by weight of citric acid based upon the total weight of the composition, and (d) from about 0.0001% to about 0.4% by weight of a metal chlorite based upon the total weight of the composition, such that the chlorite ion concentration in the form of chlorous acid is no more than about 15% by weight of the total amount of chlorite ion concentration.

18. The process of any one of claims 14 through 17 wherein the metal chlorite is sodium chlorite.

19. The process of any one of claims 14 or 16 wherein the organic acid is selected from the group consisting of malic acid, tartaric acid, glycolic acid, mandelic acid, malicylic acid, carbonic acid and combinations thereof.

20. The process of any one of claims 14 or 16 wherein the organic acid is malic acid.

21. The process of any one of claims 14 or 16 wherein the organic acid is tartaric acid.

22. The process of any one of claims 14 or 16 wherein the organic acid is glycolic acid.

23. The process of any one of claims 14 or 16 wherein the organic acid is mandelic acid.

24. The process of any one of claims 14 or 16 wherein the organic acid is salicylic acid.

25. The process of any one of claims 14 or 16 wherein the organic acid is carbonic acid.

26. The process of any one of claims 14 through 17 wherein the flavoring agent is selected from the group consisting of 1-carvone, aspartame, saccharin, peppermint oil, wintergreen oil, cinnamon oil, clove oil, menthol, thymol, eucalyptol and combinations thereof.

* * * * *

UNITED STATES PATENT AND TRADEMARK OFFICE
CERTIFICATE OF CORRECTION

PATENT NO. : 5,100,652

DATED : March 31, 1992

INVENTOR(S) : Robert D. Kross et al.

It is certified that error appears in the above-identified patent and that said Letters Patent is hereby corrected as shown below:

In column 10, claim 2, line 10, please delete "0.001%" and substitute therefor -- 0.0001% --.

In column 10, claim 6, line 45, please delete "he" and substitute therefor -- the --.

In column 11, claim 15, line 16, please delete "an organic" and substitute therefor -- citric --.

In column 12, claim 19, line 19, please delete "malicylic" and substitute therefor -- salicylic --.

Signed and Sealed this

Sixth Day of July, 1993

Attest:

MICHAEL K. KIRK

*Attesting Officer*     *Acting Commissioner of Patents and Trademarks*